US011369715B2

United States Patent
Behrens et al.

(10) Patent No.: US 11,369,715 B2
(45) Date of Patent: Jun. 28, 2022

(54) METHOD FOR PRODUCING A BIOCOMPATIBLE MATRIX WITH TARGETED STRUCTURAL DESIGN

(71) Applicant: MEDSKIN SOLUTIONS DR. SUWELACK AG, Billerbeck (DE)

(72) Inventors: Daniel Timo Behrens, Nottuln (DE); Michael Kunz, Münster (DE)

(73) Assignee: MEDSKIN SOLUTIONS DR. SUWELACK AG, Billerbeck (DE)

( * ) Notice: Subject to any disclaimer, the term of this patent is extended or adjusted under 35 U.S.C. 154(b) by 0 days.

(21) Appl. No.: 15/775,115

(22) PCT Filed: Nov. 9, 2016

(86) PCT No.: PCT/EP2016/077111
§ 371 (c)(1),
(2) Date: May 10, 2018

(87) PCT Pub. No.: WO2017/081067
PCT Pub. Date: May 18, 2017

(65) Prior Publication Data
US 2018/0326116 A1    Nov. 15, 2018

(30) Foreign Application Priority Data
Nov. 10, 2015 (EP) .................................. 15193974

(51) Int. Cl.
*A61L 27/24* (2006.01)
*A61L 27/56* (2006.01)
(Continued)

(52) U.S. Cl.
CPC ............ *A61L 27/24* (2013.01); *A61L 27/50* (2013.01); *A61L 27/56* (2013.01); *A61L 27/60* (2013.01)

(58) Field of Classification Search
None
See application file for complete search history.

(56) References Cited

U.S. PATENT DOCUMENTS 2,698,463 A * 1/1955 Conwell ................. B29C 55/02
264/210.6
3,110,549 A * 11/1963 Cohen ....................... G01K 1/14
264/212

(Continued)

FOREIGN PATENT DOCUMENTS

GB          1234358 A        6/1971

OTHER PUBLICATIONS

Zenith Applications for Plastic Extrusion, Zenith Pumps, and available online Nov. 20, 2012). (Year: 2012).*

(Continued)

*Primary Examiner* — Melissa S Mercier
(74) *Attorney, Agent, or Firm* — Medler Ferro Woodhouse & Mills PLLC

(57) ABSTRACT

The present invention relates to a method for the production of a biocompatible matrix the method comprising: a) providing a composition comprising at least one biopolymer; b) extruding the composition into a layer through a slit onto a surface, wherein the slit moves over the surface; c) optionally freezing the layer; d) optionally repeating the process to add one or more further layers; e) freezing the composition or compositions after extrusion; f) optionally drying the frozen composition wherein preferably the surface can be cooled. The invention further relates to a biocompatible matrix obtainable by the method as well as to the use of a matrix obtainable by the method for medical or cosmetic purposes. Moreover, the present invention also relates to a device for the production of a biocompatible matrix, comprising: a) a temperature controlled surface; b) an extruding means with a slit positioned above the surface; c) means for (Continued)

Figure 1:
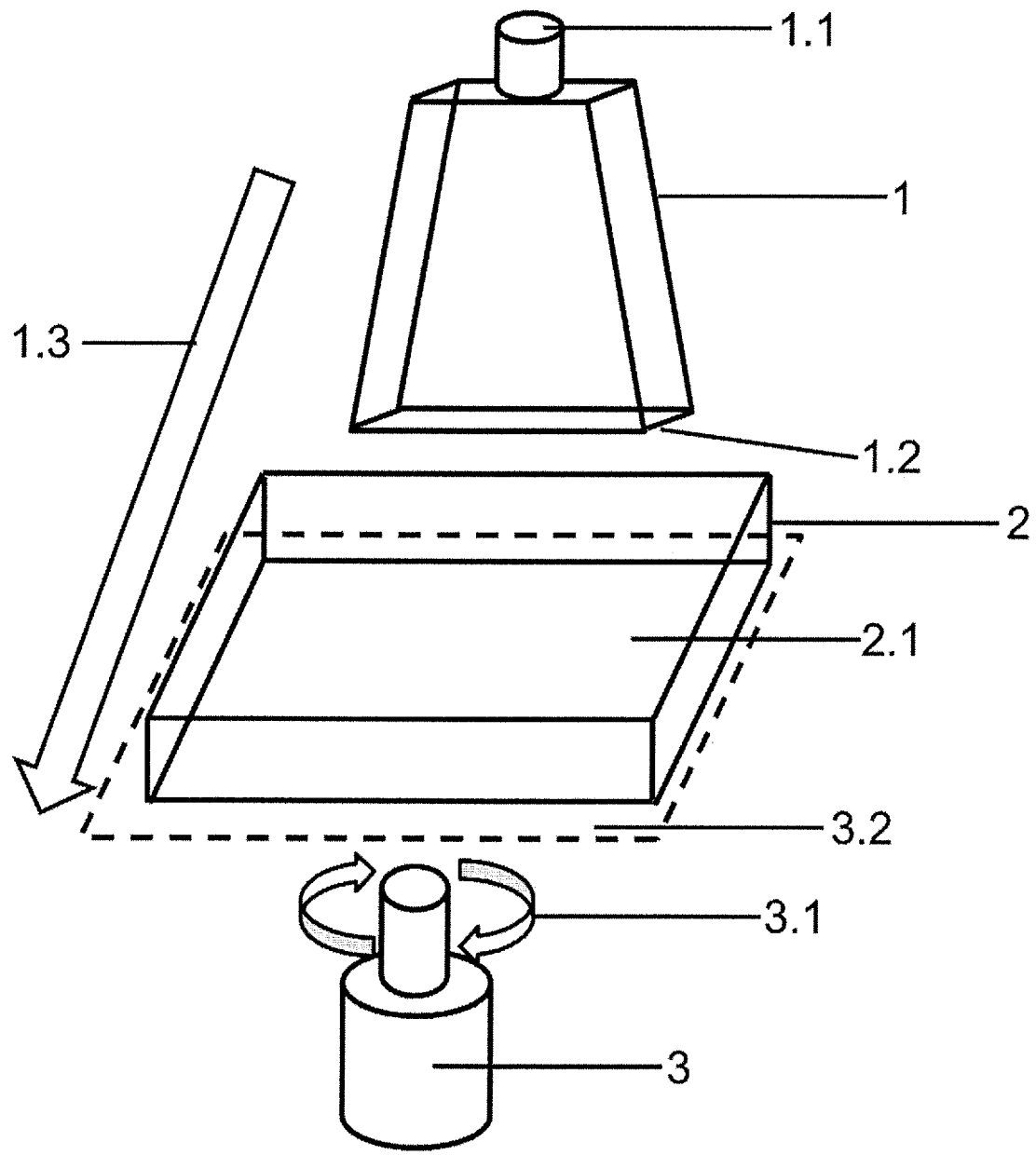

extruding a composition through the slit; d) means for moving the slit and/or the surface.

15 Claims, 3 Drawing Sheets

(51) Int. Cl.
*A61L 27/60* (2006.01)
*A61L 27/50* (2006.01)

(56) References Cited

U.S. PATENT DOCUMENTS

| | | | | |
|---|---|---|---|---|
| 4,053,270 | A | * | 10/1977 | Collier .................. B29C 48/865 425/144 |
| 4,790,167 | A | * | 12/1988 | Gentry .................... B21C 29/00 72/257 |
| 4,879,177 | A | * | 11/1989 | Boice .................... B29C 55/023 428/339 |
| 5,229,497 | A | * | 7/1993 | Boni .................. A22C 13/0016 530/356 |
| 8,940,335 | B2 | * | 1/2015 | Goessl .................... A61K 9/146 424/492 |
| 2003/0031776 | A1 | * | 2/2003 | Thresher ................. A23L 11/05 426/578 |
| 2006/0165833 | A1 | * | 7/2006 | Muschalik .............. B21C 35/02 425/296 |
| 2006/0229493 | A1 | * | 10/2006 | Weiser ............. A61B 17/00234 600/37 |
| 2007/0172533 | A1 | * | 7/2007 | Pinchot .................. B21C 35/02 425/142 |
| 2009/0306464 | A1 | * | 12/2009 | Griguol ................ A61F 2/0045 600/37 |
| 2013/0197662 | A1 | | 8/2013 | Kew et al. |
| 2014/0287006 | A1 | | 9/2014 | Malessa et al. |
| 2014/0336557 | A1 | * | 11/2014 | Durdag ............... A61F 13/0216 602/48 |

OTHER PUBLICATIONS

European Patent Office. European Search Report and Written Opinion dated Nov. 1, 2017. International Application No. PCT/EP2016/077111. International Filing Date: Nov. 9, 2016. English Language. 11 pages.

Cavallo F et al., Vaccination for treatment and prevention of cancer in animal models. Adv Immunol. 2006. 90:175-213. Review.

O'Hagan D T, et al., MF59 is a safe and potent vaccine adjuvant for flu vaccines in humans: what did we learn during its development? Clin Pharmacol Ther. Dec. 2007; 82(6):740-4.

Clapp T, et al., Vaccines with Aluminum-Containing Adjuvants: Optimizing Vaccine Efficacy and Thermal Stability., J Pharm Sci. Feb. 2011; 100(2):388-401.

Hoft D F, et al., A new recombinant bacille Calmette-Guérin vaccine safely induces significantly enhanced tuberculosis-specific immunity in human volunteers., J Infect Dis. Nov. 15, 2008; 198(10):1491-501.

Houston et al., Protein engineering of antibody binding sites: recovery of specific activity in an anti-digoxin single-chain Fv analogue produced in *Escherichia coli*. Proc. Natl. Acad. Sci. USA 1988, 85:5879-5883.

Bird et al., Single-chain antigen-binding proteins., Science 1988, 242:423-426.

International Report on Patentability issued for Application No. PCT/US2016/061062, dated May 24, 2018.

* cited by examiner

METHOD FOR PRODUCING A BIOCOMPATIBLE MATRIX WITH TARGETED STRUCTURAL DESIGN

FIELD OF THE INVENTION

The present invention is in the field of biopolymers, in particular in the field of biopolymer-based matrices. Furthermore, the invention relates to the production of biopolymer-based matrices and the use of biopolymer-based matrices, in particular the medical and cosmetic use of biopolymer-based matrices.

BACKGROUND

Biopolymer-based matrices are an essential basis for several medical and cosmetic products, such as on the one hand wound dressings, implantable scaffolds for tissue regeneration and on the other hand cosmetic masks, gels or thickening agents in serums or creams.

Many of these biopolymer-based matrices are based on the biopolymer collagen. Alternative biopolymers include hyaluronic acid, elastin, fibronectin, perlecan, aggrecan or laminin. The properties and uses of said matrices vary, depending on the biopolymer used as basis.

Biopolymer-based matrices have several advantages compared to matrices based on artificial materials such as silicone, polyesters or poly(meth)acrylic polymers, which provide a structural and/or mechanical function without inducing foreign body response but do not provide any biological stimulation of the organism to interact with the scaffold (e.g. cell colonization).

Matrices based on artificial polymers, such as silicones, allow a better control over the polymer properties, based on the composition of artificial polymers. Several properties of the matrix can be controlled.

The use of biopolymers in a matrix is challenging due to the complexity of the biological system. Therefore, one task of the present invention was the provision of a method for the generation of biopolymer-based matrices with improved properties by using the natural inherent structural advantages.

BRIEF DESCRIPTION OF THE INVENTION

The present invention relates to a method for the production of a biocompatible matrix the method comprising:
a) providing a composition comprising at least one biopolymer;
b) extruding the composition into a layer through a slit onto a surface, wherein the slit moves over the surface;
c) optionally freezing the layer;
d) optionally repeating the process to add one or more further layers;
e) freezing the composition or compositions after extrusion;
f) optionally drying the frozen composition
wherein preferably the surface can be cooled.

The invention further relates to a biocompatible matrix obtainable by the method as well as to the use of a matrix obtainable by the method for medical or cosmetic purposes.

DETAILED DESCRIPTION OF THE INVENTION

Biopolymer-based matrices are an important basis for many cosmetic or medical products, such as implants, wound dressings or facial masks. It is therefore essential that the properties of the matrices are adaptable to the intended use. The inventors have developed a method, which allows adapting the properties of a biopolymer-based matrix easily for many different applications.

Accordingly, the invention relates to a method for the production of a biocompatible matrix with adaptable and/or improved properties, the method comprising:
a) providing a composition comprising at least one biopolymer;
b) extruding the composition into a layer through a slit onto a surface, wherein the slit moves over the surface;
c) optionally freezing the layer;
d) optionally repeating the process to add one or more further layers;
e) freezing the composition or compositions after extrusion;
f) optionally drying the frozen composition.
wherein preferably the surface can be cooled.

The inventors surprisingly found that the properties of a biopolymer-based matrix produced with the method can be adjusted by the appropriate selection of the process parameters. With the above method it is possible to directionally adapt tensile strength, biodegradability of the matrix, plastic deformation or the elastic modulus of the biopolymer-based matrix.

In the context of the present invention, biopolymers are polymers produced by living organisms and/or mimicking such. In the present invention the term "biopolymer" encompasses all naturally occurring modifications of biopolymers, e.g. glycosylation, partial hydrolysis or the attachment of lipids to polypeptides, but is not limited to those.

Non-limiting examples for biopolymers according to the present invention comprise: collagens, starch, cellulose derivatives, glucosaminoglycans, alginates, polysaccarides or fucoidanes.

The matrix might be based on any biopolymer. It is however preferred that said at least one biopolymer used in the method comprises a characteristic suprastructural organisation of components, e.g. (micro) fibrils, fibers or networks. In a preferred embodiment of the invention the characteristic suprastructural organisation is a fiber/fibril structure.

The biopolymer is provided in a composition. Said composition might comprise a purified and/or modified biopolymer. However, said composition might comprise a native biopolymer. The composition might comprise further components. In one embodiment the composition additionally comprises proteins, glycoproteins, proteoglycans, polysaccharides and/or glucosaminoglycans, such as hyaluronic acid. In a preferred embodiment the composition is a naturally existing composition or derived from a naturally existing composition.

In one embodiment of the invention said composition is or comprises a biologically derived tissue and/or tissue component, comprising said biopolymer. In a preferred embodiment the composition comprising at least one biopolymer is or comprises a biologically derived tissue or tissue component selected from the group comprising bovine, equine, porcine, rodent, piscine tissue, preferably skin, tendon or cartilage tissue, most preferably bovine split skin tissue.

In one embodiment of the invention the biologically derived tissue or tissue component is not modified or processed prior to use. In a preferred embodiment the biologically derived tissue has been processed prior to its use in the method. In one embodiment minor processing, such as addition of water, washing, dilution, and/or chemical treatment on the biologically derived tissue or tissue component has been performed. In an alternative embodiment substantial processing, such as mechanical breakup of the raw material, isolation, purification, addition of water, washing, dilution, chemical treatment with acids, alkaline or oxidants, pH-adjustment, mechanical treatment and/or mechanical breakup (e.g. by mixing, mincing, milling, cutting, die-cutting), freezing and/or defrosting, has been performed.

In one embodiment of the invention, step b) involves the use of biological derived tissue(s) as composition and extrusion is performed by means of depositing said biological derived tissue(s).

In a preferred embodiment, said deposition is performed involving the folding of said biological derived tissue(s). In a more preferred embodiment, the deposition is performed by means of assembling of said biological derived tissue(s) to a multi-layered three-dimensional structure.

In a most preferred embodiment, said deposition involves mechanical treatment of biological derived tissue(s) by means of planarisation, cutting, die-cutting, embossing, slitting, generation of holes.

In an alternative preferred embodiment, said deposition involves mechanical treatment of biological derived tissue(s) by means of one- or two-dimensional shaping, e.g. in the plane of the matrix or over a 3D-template.

In an alternative embodiment a purified biopolymer is used and the composition is an artificial composition. In one embodiment the composition mimics a biological composition.

In a preferred embodiment of the invention the biopolymer is a biopolymer naturally occurring in a biologically derived tissue. In a more preferred embodiment the biopolymer is selected from the group comprising collagen, elastin, fibronectin, perlecan, aggrecan, laminin, hyaluronic acid.

In the most preferred embodiment of the invention the at least one biopolymer is collagen, more preferably bovine collagen.

In one embodiment of the invention the biopolymer is an artificially or biotechnologically generated analog of the biopolymer.

The biopolymer might be processed with methods known to the person skilled in the art, in order to extract or optimize the biopolymer. Potential treatments include but are not limited to:
  Addition of water
  Chemical treatment with acids, alkaline and oxidants with or without mechanical forces (e.g. rotation)
  Washing
  pH-adjustment
  Mechanical treatment and/or mechanical breakup (e.g. by mixing, mincing, milling, (Die-) cutting)
  Freezing
  Defrosting
  (Die-)Cutting into desired segment or shape
The biopolymer might be processed with a combination of two or more treatments.

Most preferably the biopolymer has been prepared as follows:
  Isolation and purification of collagen from bovine dermis by chemical treatment with acid, alkaline and/or oxidative agents
  Mincing of chemically treated material
  Milling resulting in a collagen dispersion In another embodiment, the composition comprises biologically derived tissue that has been prepared as follows:
  Purification of the tissue by mild chemical treatment with acid, alkaline and/or oxidative agents
  Optional (Die-)cutting into desired segment or shape
  Optional shaping by mechanical forces (planar or 3D template) and subsequent freezing under force
  Optional mechanical shaping in frozen state e.g. (cryo) cutting, CNC milling, grinding The composition should be preferably a composition with high viscosity. It is not important whether the composition comprises a naturally high viscosity or if the composition comprises additional compounds which increase the viscosity, such as hyaluronic acid, cellulosic polymers and/or synthetic hydrophilic polymers.

In another embodiment, the viscosity is adapted by dilution. In another embodiment the particle size and therefore the viscosity was changed without adding additional components for example by milling.

The composition comprising the at least one biopolymer might comprise further components, which influence the properties of the matrix or contribute to the intended use. Non-limiting examples for suitable additional components are: pharmaceutically and/or cosmetically acceptable dyes and coloring agents, medically active ingredients, compounds that improve product performance or properties e.g. biocompatibility, biodegradability, mechanical properties, sensorial properties, promotion of wound healing and tissue regeneration, anti-oxidative properties and/or water binding capacity.

Medically active compounds, suitable for addition to the composition include, but are not limited to, anesthetics, such as lidocaine and other agents that prevent transmission of nerve impulses, salicylates, Diclofenac, analgesics, antibiotics or antibiotic compounds, antimicrobials or antimicrobial compounds such as silver and silver salts, vitamins and antioxidants, compounds improving or promoting self-healing, such as panthenol, biologically active compounds such as growth factors.

The inventors found that the method of extrusion of the composition directly influences the physico-chemical properties of the matrix. The inventors surprisingly found that extrusion through a slit, preferably 0.5 to 5 mm wide and variable in length allows an ordered deposition of the characteristic structure of the biopolymer, which influences the properties of the matrix.

Preferably the slit has a width of 0.5 to 5 mm. In a preferred embodiment the slit has a width between 1 and 3 mm. The length of the slit is also variable, preferably in the range 1 to 100 cm. Most preferably, the slit length is in the range of 20 to 60 cm.

In one embodiment the surface is a mold. In a preferred embodiment the surface or mold has a specified topography. In a more preferred embodiment said specified topography comprises one or more than one of the following topological structures: flat surface, planar structure, non-planar structure, continuous structure, non-continuous structure, fillet, channel, platform, hole, pin, honeycomb, and network or a combination thereof.

In a preferred embodiment of the invention the mold allows horizontal rotation to adapt extrusion direction.

In order to extrude the composition on a surface or into a mold, the slit should be moving. The slit should preferably move in a straight line. The thickness of the layer derived from the composition and thereby some properties of the matrix can be controlled with the speed of the movement of the slit and the pressure of extrusion.

In a preferred embodiment the extrusion is performed in longitudinal orientation to the mold defining the later shape and orientation of the produced biocompatible matrix. In an alternative preferred embodiment the extrusion is performed in orthogonal orientation to the mold defining the later shape and orientation of the produced biocompatible matrix (see FIG. 2), thus creating a flat, preferably rectangular layer, or the composition of layers.

In general a faster moving slit will create a thinner layer, while a slow moving slit will produce a thicker layer, provided a constant pressure and flowrate.

It is possible to vary the movement speed of the slit, the size and shape of the slit and the flow rate of the composition, in order to create a matrix with varying thickness, e.g. a matrix comprising predetermined breaking points.

The composition is extruded by application of pressure enabling the extrusion of composition with adaptable flow rates. In one embodiment of the invention the composition is extruded using only gravity pressure, i.e. no application of external pressure. In a preferred embodiment the composition is extruded using mechanical pressure, e.g. by providing a pump. In a more preferred embodiment said pump additionally supplies a steady supply of the composition.

Any method to apply pressure is suitable to extrude the composition, preferably the pressure is controllable.

In one embodiment of the invention the composition is extruded using constant pressure. In an alternative embodiment of the invention the composition is extruded using a variable pressure.

In a most preferred embodiment the thickness of the layer of the composition is controlled by a combination of the parameters, slit speed, slit width and extrusion pressure.

In one embodiment the extruded layer of the composition has a uniform thickness. In an alternative embodiment the extruded layer has a variable thickness. In one embodiment an extruded layer has a thickness of between 3 mm to 5 cm. In a preferred embodiment the layer has a thickness of between 3 mm to 40 mm. More preferably a layer has a thickness between 5 and 25 mm and most preferably a layer has a thickness between 7.5 and 15 mm.

In one embodiment of the invention, the composition is extruded on a surface. In a preferred embodiment the surface can be cooled. In an even more preferred embodiment the surface can cool the composition below freezing temperature.

The extrusion might occur at any temperature suitable for the biopolymer. In one embodiment of the invention the extrusion is performed at room temperature. In a preferred embodiment the extrusion is performed at 0 to +40° C. In one embodiment, the surface or mold has a temperature between −80 and +40° C.

In one embodiment the surface, on which the composition is extruded, is a mold. The mold might have any shape, though a rectangular shape is preferred. In a preferred embodiment the length of the slit for extrusion is adapted to the mold.

Extrusion into a layer can be performed simultaneously to cooling or freezing of the nascent layer or the extruded layer can be cooled or frozen after completion of extrusion of said layer. Further layers might be added before or after complete freezing of respective previous layers.

In one embodiment of the invention the biocompatible matrix is based on a single layer. In an alternative embodiment the matrix is based on multiple layers. In a particular embodiment of the invention the method involves the repetition of the extrusion step to add one or more further layers.

Further layers might be added the same way as the first layer, preferably by extrusion through a slit. Said layers might consist of an identical composition as the first layer or consist of a different composition. In one embodiment of the invention all layers comprise the same biopolymer. In an alternative embodiment, at least one layer comprises a different biopolymer. Extrusion of different layers can be achieved by using an extrusion device with separate slits or separate extrusion devices.

Even if biopolymers in the layers are identical, the compositions of the layers might be different in order to adapt matrix properties to the future use of the matrix. As such, the different layers might be based on the same basic biopolymer, but for example, one layer comprises a compound with antimicrobial activity, and a second layer might only comprise a coloring agent.

The thickness of the matrix depends on the thickness of the layers. In one embodiment the matrix has a total thickness between 3 mm to 40 mm. In a preferred embodiment the matrix has a total thickness between 5 to 25 mm. In a preferred embodiment the matrix has a thickness between 7.5 mm to 15 mm before any drying step.

Figure 2:
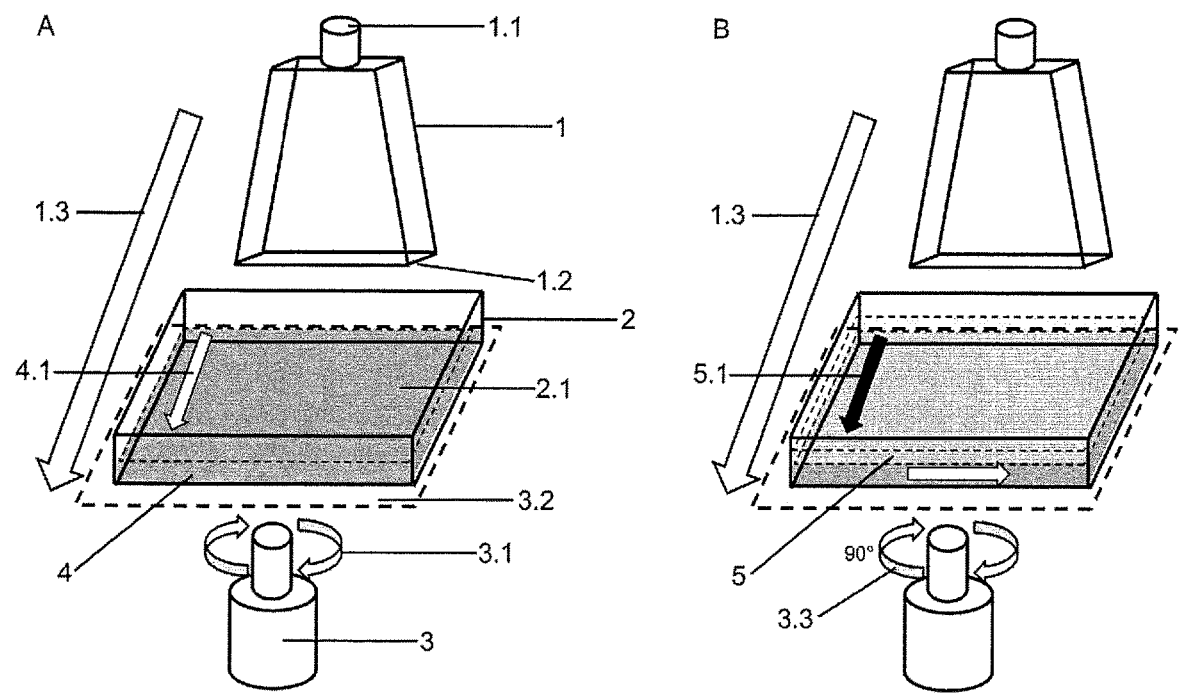

Depending on the composition and intended use of the matrix, further layers might be added in different orientations than the first layer (see FIG. 2).

FIG. 2 shows:
1 Extrusion device
  1.1 Inlet port for composition
  1.2 Slit variable in size and shape
  1.3 Movement of extrusion device
2 Mold variable in size and shape
  2.1 Bottom surface of mold variable in topography, optionally cooled
3 Device allowing variable movement of mold, e.g. motor
  3.1 Motor with rotational movement
  3.2 Optional surface, e.g. table for mold. Surface is movable by 3 and optionally cooled
  3.3 Device of 3 used for rotational movement of mold for 90° relative to initial mold orientation
4 First layer prepared by extrusion of composition through slit
  4.1 First layer obtained by longitudinal direction of extrusion relative to initial mold orientation
5 Second layer deposited on top of the first layer by extrusion of composition through slit
  5.1 Second layer obtained by orthogonal/transverse direction of extrusion relative to initial mold orientation In one embodiment of the invention, all layers are extruded in the same orientation relative to the first layer. In an alternative embodiment one or more layers are extruded orthogonal to the first layer.

The method allows the creation of improved one-dimensional tensile strength. By adapting the orientation of further layers, the tensile strength in multiple directions can be increased. Preferably the composition of the layers and the biopolymer in each layer are identical for multiple layers. In one embodiment the compositions comprising the at least one biopolymer are identical for all layers.

The inventors found that it is essential to freeze the extruded composition in the layer prior to an optional drying step. It is important that, e.g. if lyophilization is used for drying, the composition is frozen beforehand and not at the same time.

If the composition comprises multiple layers, it is possible to extrude and deposit all layers and freeze the whole base matrix or to extrude and freeze single layers. In one embodiment of the invention, each layer is frozen after extrusion before a new layer is extruded. In an alternative embodiment several layers are extruded and the composition is frozen after at least two layers have been extruded. After freezing of the first layers, subsequent layers might be added and frozen in any order. Hereby, the expression 'freezing' also comprises partial freezing, i.e. that liquid material is remained in a partially frozen layer, ensuring proper adhesion to other layers.

The inventors found that the freezing process influences the properties of the matrix. In one embodiment, the composition is shock-frozen after extrusion. In an alternative embodiment, the composition is slowly frozen after extrusion.

Cooling or Freezing can be performed with low or high cooling rates. Modification of the cooling- or freezing-kinetics enables the adaption of crystal size. Higher cooling rates result in smaller crystals. Crystal size determines the later porosity of the biocompatible matrix.

The freezing process might be performed by any suitable process. In a preferred embodiment the composition is extruded onto a cooled surface or in a cooled mold. In an alternative embodiment the composition is extruded in a mold and then frozen in a freezer providing a matrix/air interface or in liquid nitrogen.

After freezing the extruded composition has to be dried. Any drying process is suitable as long as it is compatible with the biopolymer used in the composition. In a preferred embodiment drying is performed with lyophilization.

In one embodiment of the invention the matrix is processed prior to drying. In one embodiment said processing involves mechanical shaping of frozen whole base matrix. In a particular embodiment mechanical shaping is performed by means of plaining, slitting, cutting, cryo-cutting, die-cutting, CNC milling, grinding, generation of holes.

Lyophilization of the compositions provides the additional advantage, that the composition maintains the basic shape and alignment of the characteristic structure of the biopolymer, as well as its authentic structural properties.

Targeted adaption of the lyophilisation process parameters is essential for determining later characteristics of the biocompatible matrix. For example, lyophilisation temperature has an impact on dehydrothermal crosslinking density resulting in different mechanical (e.g. tensile strength, elastic modulus) and biological properties (e.g. cell migration, biodegradability).

In an alternative embodiment the biocompatible matrix is dried by thermic drying.

The present invention further relates to biocompatible matrices obtainable by the above described method.

Said biocompatible matrices may comprise one or more layers consisting of a composition comprising a biopolymer as described above.

The inventors found that biocompatible matrices obtained by a method according to the invention show improved properties when compared to matrices of prior art. For example, a collagen based matrix produced with methods according to the invention shows adaptable tensile strength, elongation properties and elastic modulus, as well as reduced plastic deformation dependent on extrusion orientation in contrast to known matrices.

The inventors found that in particular matrices based on fiber- and/or fibril forming biopolymers show improved properties, as the directed extrusion through the slit generates a preferred structural alignment, thus improving properties like tear strength, elastic modulus and elongation, puncture resistance and plastic deformation.

Depending on the selected biopolymer and other compounds in the composition or compositions if the matrix is based on more than one layer, other properties of the matrix might be enhanced. The inventors found that biocompatibility, increased or reduced biodegradability, modified cell migration properties and an adaptation of the foreign body response can be modified with the inventive method.

The biocompatible matrices according to the invention might be directly used or might be further modified. One example of further modification is cross-linking of said biopolymer. The person skilled in the art will realize the possibilities of further physical and chemical modifications.

Potential physical modifications of the dried product include, but are not limited to: cutting, mincing, subjecting to pressure, embossing and/or three dimensional shaping.

Said matrices may also be used without further processing. The person skilled in the art will immediately realize that the matrices according to the invention are suitable for several applications. Preferably the matrices are used in cosmetic products or medical devices.

Therefore, the invention further relates to the use of a matrix according to the invention as a medical device or cosmetic product.

Preferably matrices according to the invention are used in fields of clinical applications selected from the group comprising abdomen, breast, tendon, rotator cuff, ligament, ocular, pericard, dura mater, artery, dental, facial, trauma surgery, minimally invasive surgery.

The matrices according to the invention are suitable for clinical treatment goals selected from the group comprising mechanical support, mechanical reinforcement, augmentation, repair, reconstruction, regeneration, defect closure, promotion of healing.

In a preferred embodiment the matrix is used as a medical implant. In a more preferred embodiment the matrix according to the invention is used as a biodegradable implant.

The present invention relates to a device which is suitable for the production of biocompatible matrices according to the invention. As such, the invention relates to a device for the production of a biocompatible matrix, comprising:
  a) a mold or surface;
  b) an extruding means with a slit positioned above the mold or surface;
  c) means for extruding a composition through the slit;
  d) means for moving the slit and/or the mold or surface.

In a preferred embodiment the device comprises a mold. In a more preferred embodiment the mold or surface can be cooled or refrigerated. In a more preferred embodiment the mold is able to freeze a composition. In one preferred embodiment the mold is capable to freeze a composition at high cooling rate. In an alternative preferred embodiment the mold is capable to freeze at low cooling rate. In a most preferred embodiment the mold is capable to provide variable time-dependent cooling rates.

A variable cooling rate within the meaning of this invention refers to a cooling rate of 40 to 300° C./h. In a preferred embodiment, the cooling rate is from 60 to 250° C./h, more preferably from 100 to 200° C./h.

The device should be able to extrude a composition through a slit. Suitable means are apparent to the person skilled in the art. In a preferred embodiment the device comprises a reservoir above the slit and the extruding means is gravity. In an alternative embodiment of the invention the composition is pumped through the slit. In this embodiment the device additionally comprises a pump.

In an embodiment, wherein the device according to the invention comprises a pump, it is preferred that the pump allows a steady extrusion of the composition. In a preferred embodiment the extruding means allows extrusion of the composition with constant pressure. In an alternative embodiment the extruding means allows extrusion of the composition with variable pressure.

As described above the biocompatible matrix may have a uniform or variable thickness. The device according to the invention allows modifying the thickness of the extruded layers. One method is to modify the extrusion pressure (see above).

In one embodiment of the invention the device allows the modification of the slit width. Preferably the width of the slit can be modified during extrusion. In one embodiment the slit width might be adjusted between 0.5 to 5 mm, preferably between 1 to 3 mm.

In order to provide a biocompatible matrix according to the invention it is necessary that the slit and the extrusion of the layer is moving over the mold. This might be achieved by moving the slit, the mold or both.

A preferred device according to the invention comprises a moveable slit. In a more preferred embodiment the speed of movement of the slit is variable. In an alternative variant the mold is moveable. In a preferred embodiment the mold is moveable in one or more than one direction and might be turned in place. In a most preferred embodiment the slit and mold are moveable. A schematic representation of a preferred embodiment of a device according to the invention can be found in FIG. 1. The figure shows:

1 Extrusion device
   1.1 Inlet port for composition
   1.2 Slit, variable in size and shape
   1.3 Movement of extrusion device
2 Mold variable in size and shape
   2.1 Bottom surface of mold variable in topography, optionally cooled
3 Device allowing variable movement of mold, e.g. motor
   3.1 Motor with rotational movement
   3.2 Optional surface, e.g. table for mold. Surface is movable by (3) and optionally cooled.

EXAMPLES

Collagen was extracted and purified from bovine dermis by means of acidic, alkaline and oxidative treatment. The purified collagen was minced and milled to a homogeneous collagen dispersion of medium viscosity. The collagen dispersion was used as composition for extrusion at constant flow rate and slit movement velocity at room temperature producing collagen layers according to the invention. Molds defining later matrix shape and orientation were placed longitudinally or orthogonally to slit movement direction. Layers were frozen at −45° C. and lyophilized. Specimen for mechanical testing were cut out of the lyophilized layers.

Figure 3:
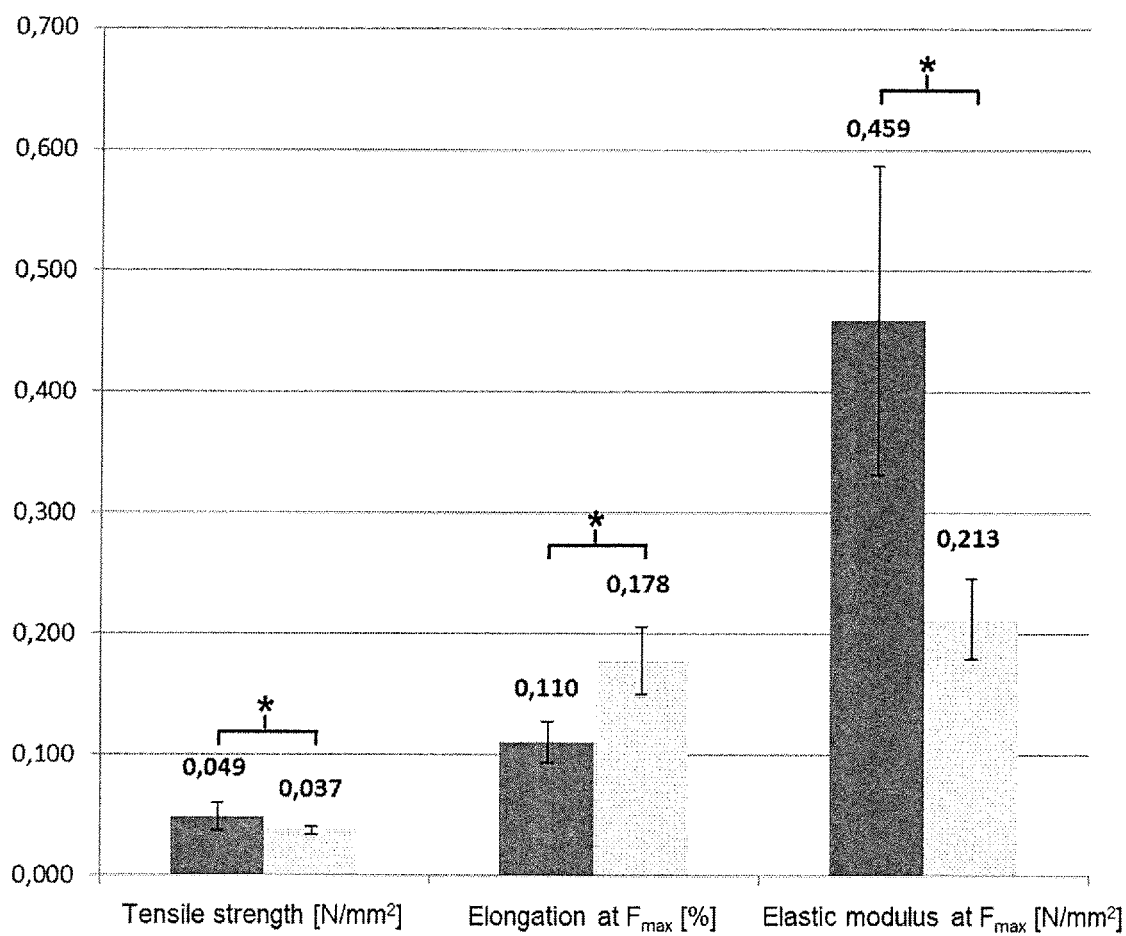

FIG. 3 shows the different properties of matrices according to the present invention. The matrices consist of two layers. The matrices were obtained by extruding the composition for both layers longitudinally (dark grey) or orthogonally (light gray) regarding mold orientation defining later matrix dimension and orientation.

It is evident that the method results in orientation-dependent tear strength, elastic modulus and elongation. Matrices show significant differences regarding the biomechanical performance parameters tensile strength, elongation and elastic modulus. Matrices obtained by longitudinal extrusion show a higher tensile strength compared to matrices produced by orthogonal extrusion. By longitudinal extrusion produced matrices are also stiffer and therefore possess a higher elastic modulus. The elongation at maximum force ($F_{max}$) is lower for these matrices.

The data show that the properties of biocompatible matrices according to the invention can be specifically modified to desired material characteristics and intended use.

FIGURE LEGENDS

FIG. 1: Schematic drawing of a device according to the present invention.

FIG. 2: Schematic drawing of a device extruding two orthogonally oriented layers according to the present invention.

FIG. 3: Comparison of physical properties of a matrix obtained by extruding the composition longitudinally (dark grey) or orthogonally (light grey) according to the invention.

The invention claimed is:

1. A method for the production of a biocompatible matrix comprising:
   a) providing a composition comprising at least one biopolymer;
   b) extruding the composition into a first layer through a slit onto a surface, wherein the slit moves in straight lines over the surface and during the extruding the slit dimensions are modified to a width between 0.5 and 5 mm and a length between 1 and 100 cm, wherein the first layer is extruded in a longitudinal direction relative to an initial surface orientation;
   c) freezing the layer by cooling the surface;
   d) repeating a) through c) to add one or more further layers, wherein a second or more further layer is extruded in an orthogonal direction relative to the initial surface orientation;
   e) freezing the composition or compositions after extrusion; and
   f) drying the frozen composition.

2. A method according to claim 1, wherein the composition comprising a biopolymer further comprises proteins, glycoproteins, proteoglycans, polysaccharides and/or glucosaminoglycans.

3. A method according to claim 1, wherein the composition comprising at least one biopolymer is of biological or biotechnological origin, a biologically derived tissue or tissue component.

4. A method according to claim 1, wherein the composition comprising at least one biopolymer is a biologically derived tissue selected from the group of origin comprising bovine, equine, porcine, rodent, piscine tissue, skin, tendon or cartilage tissue and bovine split skin.

5. A method according to claim 1, wherein the at least one biopolymer is collagen.

6. A method according to claim 1, wherein the composition additionally comprises one or more than one cosmetically or pharmaceutically acceptable additives.

7. A method according to claim 1, wherein step f) comprises drying by lyophilization.

8. A biocompatible matrix obtainable by a method according to claim 1.

9. A device for the production of a biocompatible matrix, comprising:
   a) a temperature controlled surface;
   b) an extruder with a slit positioned above the surface, wherein the extruder is configured to modify the width of the slit to between 0.5 and 5 mm and configured to modify the length of the slit to between 1 and 100 cm during extruding;

c) a pump to extrude a composition through the slit; and
d) a motor for imparting a rotational motion to the surface and/or a linear motion to the slit.

10. A device according to claim 9, wherein the temperature-controlled surface can freeze the composition with variable cooling rate.

11. A method of preparing a cosmetic product comprising a biocompatible matrix according to claim 8, the method comprising introducing the biocompatible matrix into a mask or a gel, or formulating as a serum or cream.

12. A method of preparing a medical device comprising a biocompatible matrix according to claim 8, the method comprising application of the biocompatible matrix as part of a wound dressing or implantable scaffold.

13. A method according to claim 4, wherein the biologically derived tissue is bovine split skin.

14. A method according to claim 6, wherein the pharmaceutically acceptable additive is an antibiotic compound.

15. A method according to claim 14, wherein the antibiotic compound is silver or a silver salt.

\* \* \* \* \*